(12) United States Patent
Brisley

(10) Patent No.: US 8,512,682 B2
(45) Date of Patent: Aug. 20, 2013

(54) FOOD PRODUCT TO PREVENT TOOTH DECAY

(75) Inventor: Mark William Brisley, Laguna Beach, CA (US)

(73) Assignee: R & B Tooth Armour, LLC, Laguna Beach, CA (US)

( * ) Notice: Subject to any disclaimer, the term of this patent is extended or adjusted under 35 U.S.C. 154(b) by 184 days.

(21) Appl. No.: 12/775,292

(22) Filed: May 6, 2010

(65) Prior Publication Data
US 2010/0284947 A1    Nov. 11, 2010

Related U.S. Application Data

(60) Provisional application No. 61/176,592, filed on May 8, 2009.

(51) Int. Cl.
| | | |
|---|---|---|
| *A61Q 11/00* | (2006.01) | |
| *A23L 2/60* | (2006.01) | |
| *A61K 8/60* | (2006.01) | |

(52) U.S. Cl.
USPC ................ 424/49; 426/72; 426/117; 426/548

(58) Field of Classification Search
None
See application file for complete search history.

(56) References Cited

U.S. PATENT DOCUMENTS

| | | | | |
|---|---|---|---|---|
| 3,746,198 | A * | 7/1973 | Howland | 215/11.1 |
| 4,134,999 | A * | 1/1979 | Muhler et al. | 426/660 |
| 5,246,725 | A * | 9/1993 | Fisher et al. | 426/565 |
| 5,385,748 | A * | 1/1995 | Bunger et al. | 426/590 |
| 6,037,375 | A * | 3/2000 | Sakamoto et al. | 514/561 |
| 6,989,166 | B2 * | 1/2006 | Te Hennepe et al. | 426/2 |
| 2003/0008057 | A1 * | 1/2003 | Hynes et al. | 426/590 |
| 2007/0134391 | A1 * | 6/2007 | Prakash et al. | 426/548 |
| 2008/0226770 | A1 * | 9/2008 | Lee et al. | 426/66 |
| 2008/0226803 | A1 * | 9/2008 | Letourneau et al. | 426/597 |
| 2009/0110758 | A1 * | 4/2009 | Seed et al. | 424/738 |

FOREIGN PATENT DOCUMENTS

| | | |
|---|---|---|
| SE | 8904190 A0 * | 12/1989 |
| WO | WO 2007064222 A1 * | 6/2007 |
| WO | WO 2008044784 A1 * | 4/2008 |

OTHER PUBLICATIONS

Tezcan, F., Gultekin-Ozguven, M., Diken, T., Ozcelik, B., Erim, F.B. Antioxidant activity and total phenolic, organic acid and sugar content in commercial pomegranate juices. Food Chemistry 115 (2009) 873-877.*
Garber, L.L., Hyatt, H.M., Starr, R.G. Jr. The Effects of Food Color on Perceived Flavor. Journal of Marketing Theory and Practice, fall 2000, 59-72.*
Medline Plus Fact Sheets on Vitamins B3 , B5 , B6, B12. U.S. National Library of Medicine. Downloaded from the site: http://www.nlm.nih.gov/ on Mar. 23, 2011.*
Matsukubo, T., Takazoe, I. Sucrose substitutes and their role in caries prevention. International Dental Journal (2006), 56(3), 119-130.*
Drake, S.R., Eisele, T.A. Carbohydrate and Acid Contents of Gala Apples and Bartlett Pears from Regular and Controlled Atmosphere Storage. J. Agric. Food Chem. 1999, 47, 3181-3184.*
B.W. Li and P. J. Schuhmann, Sugar Analysis of Fruit Juices: Content and Method, Journal of Food Science, vol. 48 (1983), pp. 633-635 and 653.*
Camilla T. Damsgaard, Lotte Lauritzen, Tanja M.R. Kjær, Puk M. I. Holm, Maj-Britt Fruekilde, Kim F. Michaelsen, and Hanne Frøkiær. Fish Oil Supplementation Modulates Immune Function in Healthy Infants, J. Nutr. 137: 1031-1036, 2007.*
Hammer Nutrition, Heed Nutrition Sport Drink Mix; From: www.rei.com, www.hammernutrition.com, www.runningforums.com, and photographs of product; 18 pages.
Xlear, Inc., Xlear Xylitol Nasal Spray, Candy, and Sweetener; From: www.xlear.com; 12 pages.
Epic Industries, Epic Dental Xylitol Products; From: www.epicdental.com; 1 page.
Tapianen, Kontiokari, Sammalkivi, Ikahemio, Koskela & Uhari, "Effect of Xylitol on Growth of Streptoccus Pneumoniae in the Presence of Fructose and Sorbitol"; Antimicrobial Agents and Chemotherapy (American Society for Microbiology) Jan. 2001, p. 166-169, vol. 45, No. 1; 4 pages.

\* cited by examiner

Primary Examiner — Frederick Krass
Assistant Examiner — Michael P Cohen
(74) Attorney, Agent, or Firm — Knobbe Martens Olson & Bear LLP

(57) ABSTRACT

An anti cavity bioconsumable liquid which may be provided in the liquid form or frozen form is disclosed herein. The liquid may include up to about 5 wt. % xylitol for the purposes of mitigating tooth decay when the bioconsumable liquid is ingested or consumed by a person. Moreover, the bioconsumable liquid may include up to about 5 wt. % of dextrose but never more than the wt. % of xylitol for the purposes of sweetening the bioconsumable liquid to retain an acceptable flavor profile. An infant, child or adult may consume the bioconsumable liquid during which the xylitol acts to mitigate tooth decay. The bioconsumable liquid may also be frozen in an ice pop configuration and consumed by a child or an adult. The ice pop retains an acceptable flavor profile and also mitigates tooth decay.

12 Claims, 1 Drawing Sheet

FOOD PRODUCT TO PREVENT TOOTH DECAY

CROSS-REFERENCE TO RELATED APPLICATIONS

This application claims the benefit of U.S. Pat. App. Ser. No. 61/176,592, filed on May 8, 2009, the entire contents of which is expressly incorporated herein by reference.

STATEMENT RE: FEDERALLY SPONSORED RESEARCH/DEVELOPMENT

Not Applicable

BACKGROUND

The present invention relates generally to a flavored food product to prevent tooth decay in infants, small children and adults.

Biofilm is known to contain bacteria that produces lactic acid which can cause the demineralization of the surface of teeth, thereby resulting in tooth decay. An example of tooth decay commonly found in infants and children is baby bottle tooth syndrome. There are very few bioconsumable food products known to prevent plaque formation and tooth decay.

Accordingly, a significant need is present for an anti-cavity bioconsumable product to prevent plaque formation and tooth decay in infants, children and adults.

BRIEF SUMMARY

An anti-cavity bioconsumable product is disclosed to prevent plaque formation and tooth decay. The anti-cavity bioconsumable food product may comprise xylitol in solid form or xylitol dissolved in a consumable liquid. If xylitol is provided as an aqueous solution, the aqueous xylitol product may comprise the consumable liquid with xylitol and dextrose dissolved in the consumable liquid. More particularly, the xylitol may be up to about 5 wt. % of the aqueous xylitol product. The dextrose may also be incorporated (e.g., dissolved) into the liquid in a ratio less than or equal to 1:1 in relation to the xylitol. By way of example and not limitation, the xylitol may be about 5 wt. % of the aqueous xylitol product. In this instance, the dextrose may be about 5 wt. % or less of the aqueous xylitol product. In this manner, the aqueous xylitol product still retains significant tooth decay prevention from the xylitol and still has an acceptable flavor profile. The aqueous xylitol product may also be frozen to produce a frozen confectionery bioconsumable product (e.g., ice pop).

The aqueous xylitol product may be useful to prevent tooth decay in infants, children and adults. Additionally, the aqueous xylitol product may be provided to infants, children and adults for a liquid replenishment or beverage product such as in the form of a sports drink. Moreover, the aqueous xylitol product may be frozen into an ice cube configuration or an ice pop configuration and served to children and adults. By providing the liquid form or solid form (e.g., frozen form) of the aqueous xylitol product to infants, children and adults, tooth decay may be mitigated without any change in eating habits since the dextrose ingredient promotes an acceptable flavor profile.

Other ingredients may also be added to the aqueous xylitol product such as one or more of the following: a vitamin blend, natural flavors, colorant, citric acid, stevia and gum (e.g., guar gum, gum acacia, xanthan gum, or combinations thereof). By way of example and not limitation, the aqueous xylitol product may comprise about 97 to about 90 wt. % water, about 0.003 to about 0.001 wt. % vitamin blend, about 5 to about 1 wt. % xylitol, about 1 to about 0.01 wt. % flavoring, about 0.02 to about 0.001 wt. % citric acid, about 0.02 to about 0.001 wt. % stevia, about 5 to about 0.5 wt. % dextrose and about 0.3 to about 0.01 wt. % gum (e.g., guar gum, gum acacia, xanthan gum, or combinations thereof). The weight percentage of dextrose must be less than or about equal to the weight percentage of xylitol in the aqueous xylitol product.

More particularly, the aqueous xylitol product may be about 93.45175 wt. % water, about 0.002 wt. % B Vitamin Blend (e.g., B3, B5, B6 and B12), about 3.12 wt. % xylitol, about 0.25 wt. % Natural Apple flavor, about 0.00625 wt. % citric acid, about 0.01 wt. % stevia, about 3.00 wt. % dextrose, and about 0.10 wt. % gum (e.g., guar gum, gum acacia, xanthan gum, or combinations thereof). This embodiment of the product may further include a coloring additive of about 0.06 wt. % shade amber.

In another embodiment, the aqueous xylitol product may be about 93.43175 wt. % water, about 0.002 wt. % B Vitamin Blend (e.g., B3, B5, B6 and B12), about 3.12 wt. % xylitol, about 0.10 wt. % Natural Blueberry flavor, about 0.00625 wt. % citric acid, about 0.01 wt. % stevia, about 3.00 wt. % dextrose, and about 0.10 wt. % gum (e.g., guar gum, gum acacia, xanthan gum, or combinations thereof). This embodiment may further include the coloring additive about 0.23 wt. % shade Bordeaux.

In yet a further embodiment, the aqueous xylitol product may be about 93.54375 wt. % water, about 0.002 wt. % B Vitamin Blend (e.g., B3, B5, B6 and B12), about 3.12 wt. % xylitol, about 0.15 wt. % Natural Peach flavor, about 0.00625 wt. % citric acid, about 0.01 wt. % stevia, about 3.00 wt. % dextrose, and about 0.10 wt. % gum (e.g., guar gum, gum acacia, xanthan gum, or combinations thereof). In a further embodiment, the product may also include the coloring additive about 0.062 wt. % beta carotene 10% CWD 10% h2O. This embodiment further also include 0.006 wt. % ascorbic acid.

In a further embodiment, the aqueous xylitol product may include about 93.64175 wt. % water, about 0.002 wt. % B Vitamin Blend (e.g., B3, B5, B6 and B12), about 3.12 wt. % xylitol, about 0.12 wt. % Natural Almond Cream flavor, about 0.00625 wt. % citric acid, about 0.01 wt. % stevia, about 3.00 wt. % dextrose, and about 0.10 wt. % gum (e.g., guar gum, gum acacia, xanthan gum, or combinations thereof).

Xylitol either in solid or liquid form may be incorporated into the following food stuff: (1) liquid foodstuff including but not limited to water, milk, baby formula, and vitamin beverages and (2) solid foodstuff including but not limited to ice pop, ice cream, and gelatin. It is also contemplated that the xylitol in liquid form may be consumed as a liquid replacement drink.

While drinking liquid foodstuff or consuming solid food stuff containing the anti-cavity bioconsumable food product, plaque formation and tooth decay are being mitigated and/or prevented.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
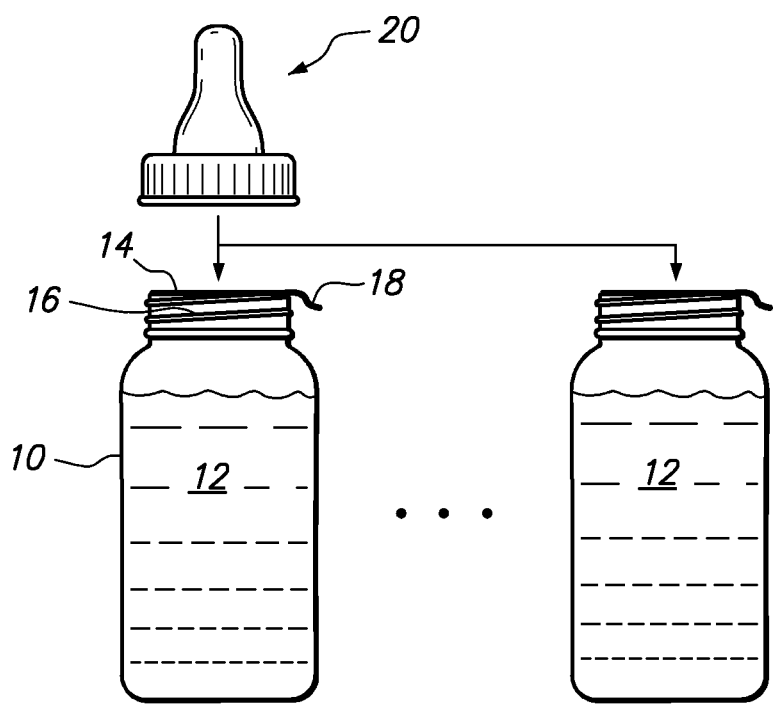
FIG. 1 is an illustration of a baby bottle with a liquid food product containing xylitol that can be attached to a baby bottle nipple cover.

The bioconsumable food product described herein contains an active ingredient for preventing tooth decay. In particular, the active ingredient may be xylitol which may be provided in solid or liquid form (e.g., xylitol dissolved in liquid). The food product may be added to various food stuffs existing in both liquid and solid form. Also, the food product may be consumed as a liquid replacement for the body. Xylitol has an active anti-caries effect that serves to block the formation of biofilm or plaque on the surface of teeth. Biofilm contains bacteria that produce lactic acid which demineralizes the surface of teeth, thereby causing tooth decay. The xylitol is a sweetener that cannot be metabolized by bacteria in the mouth thereby further preventing biofilm formation of the teeth. The prevention of the formation of biofilm on the teeth can eliminate demineralization of the tooth surface. Accordingly, tooth decay may be mitigated or even prevented with the consumption of the bioconsumable product containing xylitol.

Dextrose may also be incorporated into the bioconsumable food product containing xylitol. In all instances, the weight percent of dextrose is about equal to or less than the weight percent of xylitol contained in the bioconsumable food product. By way of example and not limitation, up to about 5 wt. % xylitol may be incorporated into the bioconsumable food product. Additionally, approximately the same or less weight percent of dextrose as xylitol may be incorporated into the bioconsumable food product. When the weight percent of dextrose is greater than the weight percent of xylitol, then the tooth decay prevention benefits of xylitol are significantly or entirely eliminated. In this manner, the xylitol serves to block the formation of biofilm or plaque on the surface of the teeth thereby mitigating tooth decay and the dextrose facilitates an acceptable flavor profile in the bioconsumable food product.

The bioconsumable food product for mitigating plaque formation and tooth decay may be provided in solid granular form or as a liquid with xylitol and dextrose dissolved within the liquid. When the bioconsumable product is provided in liquid form, the food product may comprise liquid (e.g., water), xylitol and dextrose. The liquid food product may also include one or more of the following: a vitamin blend, natural flavors, citric acid, stevia, and gum (e.g., guar gum, gum acacia, xanthan gum, or combinations thereof). The bioconsumable food product may be added to the foodstuff to sweeten the foodstuff. The sweetening of the foodstuff with the natural sweetener xylitol may improve the taste of the foodstuff so as to encourage its regular and repeated use in order to prevent tooth decay. This feature may be especially attractive to infants, children and adults, who may be more likely to consume a product that tastes good.

The food product may be also used with a liquid foodstuff such as water, milk, baby formula, and vitamin beverages, etc. The active ingredient (i.e., xylitol) may be dissolved into the liquid such that as the liquid foodstuff is consumed, the active ingredient may contact the surface of the teeth and block plaque formation. Dextrose facilitates an acceptable flavor profile for the liquid foodstuff. The user need not change their eating or oral hygiene habits. Rather, a regimen that includes the selection of one or more of these beverages may enable the reduction or elimination of plaque formation and tooth decay. The opportunity to select from a variety of flavored beverages containing the bioconsumable product and its active ingredient xylitol may serve to encourage the continuous and regular use of the bioconsumable product for its beneficial properties, especially in infants, children and adults.

With the presence of xylitol to mitigate tooth decay and dextrose as a natural sweetener in the liquid or solid food stuff to promote an acceptable flavor profile, the amount of sugar or sugar substitutes added to the liquid or solid food stuff may be reduced or eliminated. It is contemplated that the xylitol based food product may be used as the sole sweetener for the liquid or solid foodstuff.

When the xylitol based food product is used to sweeten a liquid foodstuff, xylitol may be up to about 5 wt. % of the liquid food stuff. Dextrose may also be incorporated into the liquid foodstuff up to about 5 wt. % but no more than the weight percent of xylitol. The liquid foodstuff may optionally include other additives such as vitamins, flavors (e.g., natural, artificial, etc.), citric acid and stevia. By way of example and not limitation, the liquid food stuff may include one or more of the following ingredients: about 97 to about 90 wt. % water, about 0.003 to about 0.001 wt. % vitamin blend, about 5 to about 1 wt. % xylitol, about 1 to about 0.01 wt. % flavoring, about 0.02 to about 0.001 wt. % citric acid, about 0.02 to about 0.001 wt. % stevia, about 5 to about 0.5 wt. % dextrose and about 0.3 to about 0.01 wt. % gum (e.g., guar gum, gum acacia, xanthan gum, or combinations thereof). More particularly, the composition of the aqueous bioconsumable product may include about 93.45175 wt. % water, about 0.002 wt. % B Vitamin Blend (e.g., B3, B5, B6 and B12), about 3.12 wt. % xylitol, about 0.25 wt. % Natural Apple flavor, about 0.00625 wt. % citric acid, about 0.01 wt. % stevia, about 3.00 wt. % dextrose, and about 0.10 wt. % gum (e.g., guar gum, gum acacia, xanthan gum, or combinations thereof). This embodiment may further include a coloring additive of about 0.06 wt. % shade amber.

In another embodiment, the aqueous xylitol product may be about 93.43175 wt. % water, about 0.002 wt. % B Vitamin Blend (e.g., B3, B5, B6 and B12), about 3.12 wt. % xylitol, about 0.10 wt. % Natural Blueberry flavor, about 0.00625 wt. % citric acid, about 0.01 wt. % stevia, about 3.00 wt. % dextrose, and about 0.10 wt. % gum (e.g., guar gum, gum acacia, xanthan gum, or combinations thereof). This embodiment may further include the coloring additive about 0.23 wt. % shade bordoux.

In another embodiment, the aqueous xylitol product may be about 93.54375 wt. % water, about 0.002 wt. % B Vitamin Blend (e.g., B3, B5, B6 and B12), about 3.12 wt. % xylitol, about 0.15 wt. % Natural Peach flavor, about 0.00625 wt. % citric acid, about 0.01 wt. % stevia, about 3.00 wt. % dextrose, and about 0.10 wt. % gum (e.g., guar gum, gum acacia, xanthan gum, or combinations thereof). This embodiment may further include the coloring additive about 0.062 wt. % beta carotene, about 10% CWD 10% h2O. This embodiment may also further include about 0.006 wt. % ascorbic acid.

In another embodiment, the aqueous xylitol product may include about 93.64175 wt. % water, about 0.002 wt. % B Vitamin Blend (e.g., B3, B5, B6 and B12), about 3.12 wt. % xylitol, about 0.12 wt. % Natural Almond Cream flavor, about 0.00625 wt. % citric acid, about 0.01 wt. % stevia, about 3.00 wt. % dextrose, and about 0.10 wt. % gum (e.g., guar gum, gum acacia, xanthan gum, or combinations thereof).

It is contemplated that xylitol may be added to the solid food stuff during the cooking process. Xylitol may be used as a supplemental sugar substitute or the sole sweetening additive.

In one embodiment, xylitol and dextrose may be added to liquid and/or solid food products specifically intended for consumption by infants, children and adults, such as baby formula, ice pop, gelatin, and ice cream. Also, the liquid food product containing xylitol and dextrose may be provided to recreational and professional athletes, children and adults as a sports drink. As discussed above, the addition of xylitol to these food stuffs for infants, children and adults may reduce or eliminate tooth decay in this age group without necessitating any change in eating habits or oral hygiene. Dextrose maintains an acceptable flavor profile.

Referring now to FIG. 1, xylitol may be provided to infants prior to putting the infant to bed. To this end, a baby bottle 10 may be filled with liquid food product 12. The liquid food product contains xylitol and dextrose dissolved in the liquid. The liquid food product 12 may have any formulation of the aqueous xylitol product disclosed herein or any liquid foodstuff with less than 5 wt. % xylitol and less than 5 wt. % dextrose with the weight percent of dextrose being about equal to or less than the weight percent of xylitol. Also, the liquid food product may be flavored with different fruits flavors. A protective seal 14 is placed over the opening 16 and may be peeled off by pulling on the tab 18. The baby bottle 10 may be a standard baby bottle 10 that can fit any one of a plurality of baby bottle nipple covers 20.

A parent may purchase one or more of the baby bottles 10 with liquid food product 12 disposed inside. Before the infant is put to bed, the parent may feed the baby the liquid food product 12. The parent will peel off the protective seal 14 by pulling up on the tab 18. The nipple cover 20 will be screwed onto the baby bottle 10. By feeding the infant with the liquid food product 12 which contains xylitol, the fluid is coating the teeth of the infant or small child with xylitol which mitigates tooth decay. Dextrose facilitates an acceptable flavor profile to the infant or child.

Figure 2:
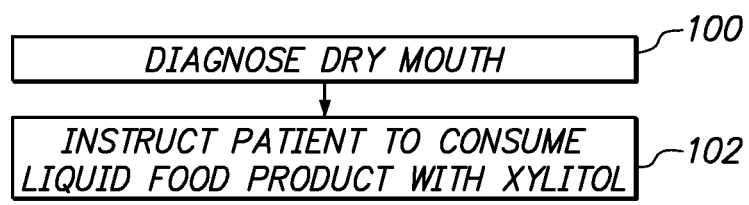
FIG. 2 is a flow chart of a process for treating dry mouth syndrome.

Referring now to FIG. 2, xylitol may be used to treat dry mouth syndrome. In particular, when a patient has dry mouth, a medical professional (e.g., nurse, doctor, etc.) may diagnose 100 that the patient has dry mouth syndrome. In order to alleviate the discomfort due to dry mouth syndrome, the medical professional may instruct 102 the patient to ingest liquid food product containing xylitol.

Other ingredients may be used in lieu of dextrose. By way of example and not limitation, sucrose and galactose may replace the dextrose. However, when sucrose and galactose are used, the xylitol to sucrose ratio must be 5:1 or less. For example, 5 wt. % of xylitol to 1 wt. % or less of sucrose. Likewise, the ratio of xylitol to galactose must be 5:1 or less. For example, 5 wt. % of xylitol to 1 wt. % or less of sucrose. Nonetheless, dextrose is the preferred combination or mixture with xylitol for retaining an acceptable flavor profile.

The above description is given by way of example, and not limitation. Given the above disclosure, one skilled in the art could devise variations that are within the scope and spirit of the invention disclosed herein, including various ways of incorporating xylitol into the solid and fluid food products. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method to mitigate plaque formation or tooth decay, comprising identifying an infant or child at risk for plaque formation or tooth decay and administering a beverage to the infant or child, the beverage having an acceptable flavor profile, the beverage comprising liquid, greater than 0 wt. % up to about 5 wt. % xylitol and greater than 0 wt. % up to 5 wt. % dextrose of the liquid wherein the wt. % of dextrose is less than the wt. % of the xylitol, and wherein the beverage is administered in an amount effective to mitigate the formation of plaque or tooth decay as compared to an infant or child not receiving said beverage.

2. The method as claimed in claim 1, wherein the liquid is selected from the group consisting of water, milk, baby formula and vitamin beverage.

3. The method as claimed in claim 1, wherein the beverage is about 93.45175 wt. % water, about 3.12 wt. % xylitol, about 0.25 wt. % Natural Apple flavor, about 0.00625 wt. % citric acid, about 0.01 wt. % stevia, about 3.00 wt % dextrose, and about 0.10 wt. % gum.

4. The method as claimed in claim 1, wherein the beverage is about 93.43175 wt. % water, about 3.12 wt. % xylitol, about 0.10 wt. % Natural Blueberry flavor, about 0.00625 wt. % citric acid, about 0.01 wt. % stevia, about 3.00 wt. % dextrose, and about 0.10 wt. % gum.

5. The method as claimed in claim 1, wherein the beverage is about 93.54375 wt. % water, about 3.12 wt. % xylitol, about 0.15 wt. % Natural Peach flavor, about 0.00625 wt. % citric acid, about 0.01 wt. % stevia, about 3.00 wt. % dextrose, and about 0.10 wt. % gum.

6. The method as claimed in claim 5 wherein the beverage further includes about 0.006 wt. % ascorbic acid.

7. The method as claimed in claim 1, wherein the beverage is about 93.64175 wt. % water, about 3.12 wt. % xylitol, about 0.12 wt. % Natural Almond Cream flavor, about 0.00625 wt. % citric acid, about 0.01 wt. % stevia, about 3.00 wt. % dextrose, and about 0.10 wt. % gum.

8. The method of claim 1 wherein the liquid with xylitol and dextrose are frozen.

9. The method of claim 1 wherein the beverage is formed into an ice pop configuration.

10. The method of claim 1 wherein wt % of dextrose is about 3 wt. %.

11. A method to mitigate tooth decay, comprising:
identifying an infant at risk for tooth decay; and
providing to the infant a baby bottle having an effective amount of a liquid food product disposed within the baby bottle;
the liquid food product comprising xylitol and dextrose dissolved in the liquid food product, the amounts of xylitol and dextrose in the liquid food product being greater than 0 wt. % up to about 5 wt. % xylitol and greater than 0 wt. % up to 5 wt. % dextrose wherein the wt. % of dextrose is less than the wt. % of the xylitol, and wherein the liquid food product is provided in an amount effective to mitigate tooth decay as compared to an infant not provided with said liquid food product.

12. The method of claim 11, the liquid food product further comprising one or more of a flavor additive, a color additive, a vitamin additive, water, citric acid, stevia, and gum.

\* \* \* \* \*